(12) United States Patent
Barretto et al.

(10) Patent No.: US 10,531,838 B2
(45) Date of Patent: Jan. 14, 2020

(54) APPARATUS, SYSTEM, METHOD AND COMPUTER PROGRAM FOR ASSESSING THE RISK OF AN EXACERBATION AND/OR HOSPITALIZATION

(71) Applicant: KONINKLIJKE PHILIPS N.V., Eindhoven (NL)

(72) Inventors: Chevone Marie Barretto, London (GB); Rita Priori, Cambridge (GB); Cees Van Berkel, Hove (GB); Mareike Klee, Straelen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 382 days.

(21) Appl. No.: 15/321,259

(22) PCT Filed: Jun. 26, 2015

(86) PCT No.: PCT/EP2015/064488
§ 371 (c)(1),
(2) Date: Dec. 22, 2016

(87) PCT Pub. No.: WO2015/197809
PCT Pub. Date: Dec. 30, 2015

(65) Prior Publication Data
US 2017/0156680 A1    Jun. 8, 2017

(30) Foreign Application Priority Data

Jun. 27, 2014  (WO) ................ PCT/CN2014/080981
Aug. 6, 2014   (EP) ..................................... 14179993
(Continued)

(51) Int. Cl.
*A61B 5/00* (2006.01)
*A61B 5/11* (2006.01)
(Continued)

(52) U.S. Cl.
CPC .......... *A61B 5/7275* (2013.01); *A61B 5/0022* (2013.01); *A61B 5/091* (2013.01);
(Continued)

(58) Field of Classification Search
CPC ....... A61B 5/11; A61B 5/1118; A61B 5/0022; A61B 5/7275; A61B 5/091
See application file for complete search history.

(56) References Cited

U.S. PATENT DOCUMENTS

| 6,108,685 A | 8/2000 | Kutzik |
| 7,589,637 B2 | 9/2009 | Bischoff |

(Continued)

FOREIGN PATENT DOCUMENTS

| JP | 2002143097 A | 5/2002 |
| JP | 2013544616 A | 12/2013 |

(Continued)

OTHER PUBLICATIONS

Moy, Marilyn L. et al., "Daily Step Count Predicts Acute Exacerbations in a US Cohort with COPD", PLOS ONE, vol. 8, No. 4, Apr. 4, 2013 (Apr. 4, 2013), p. e60400, XP055146602.

(Continued)

*Primary Examiner* — Max F Hindenburg

(57) ABSTRACT

Chronic obstructive pulmonary disease (COPD) is one of the growing chronic respiratory diseases and is now a major cause of morbidity and mortality. Acute exacerbations have a negative impact on health related quality of life of COPD patients, survival rates, pulmonary function and utilization of health-care resources. The present application discloses an apparatus (100), system (1400), method (200), and computer program for assessing a risk of an exacerbation and/or hospitalization of a subject. To this extent, time-dependent activity data is Fourier-transformed to frequency space to obtain frequency-dependent activity data. Next, a moment of
(Continued)

said frequency-dependent activity data is computed. Finally, a risk of said exacerbation and/or hospitalization of said subject to occur is assessed based on said moment.

15 Claims, 8 Drawing Sheets

(30) Foreign Application Priority Data

Aug. 6, 2014 (EP) .................................. 14179997
Aug. 8, 2014 (EP) .................................. 14180307

(51) Int. Cl.
*G16H 50/30* (2018.01)
*A61B 5/091* (2006.01)
*G06F 19/00* (2018.01)

(52) U.S. Cl.
CPC .......... *A61B 5/1118* (2013.01); *A61B 5/7257* (2013.01); *G06F 19/3481* (2013.01); *G16H 50/30* (2018.01)

(56) References Cited

U.S. PATENT DOCUMENTS

| | | | |
|---|---|---|---|
| 7,708,697 | B2 | 5/2010 | Wilkinson |
| 8,206,325 | B1* | 6/2012 | Najafi ............... A61B 5/1116 600/595 |
| 8,525,687 | B2 | 9/2013 | Tran |
| 8,585,607 | B2 | 11/2013 | Klap |
| 9,311,789 | B1* | 4/2016 | Gwin .................. G08C 19/00 |
| 9,566,004 | B1* | 2/2017 | Radwin |
| 2010/0010552 | A1 | 1/2010 | Wilson |
| 2010/0045465 | A1 | 2/2010 | Brauker |
| 2011/0034818 | A1 | 2/2011 | Gat et al. |
| 2011/0098608 | A1 | 4/2011 | Griffiths et al. |
| 2011/0125044 | A1 | 5/2011 | Rhee |
| 2011/0184250 | A1 | 7/2011 | Schmidt |
| 2012/0130201 | A1 | 5/2012 | Jain |
| 2012/0253142 | A1 | 10/2012 | Meger |
| 2013/0030258 | A1 | 1/2013 | Cheung |
| 2013/0310699 | A1 | 11/2013 | Hart |
| 2014/0012099 | A1 | 1/2014 | Halperin |
| 2017/0156681 | A1 | 6/2017 | Nijsen |

FOREIGN PATENT DOCUMENTS

| | | |
|---|---|---|
| JP | 2017522951 A | 8/2017 |
| WO | WO9712546 A1 | 4/1997 |
| WO | WO2013080109 A2 | 6/2013 |
| WO | WO2013086564 A1 | 6/2013 |

OTHER PUBLICATIONS

Dias A. et al., "Classification of Exacerbation Episodes in Chronic Obstructive Pulmonary Disease Patients", Methods of Information in Medicine, Schattauer GMBH, DE, vol. 53, No. 2, Feb. 11, 2014 (Feb. 11, 2014), pp. 108-114, XP008172454.

Dias Andre et al., "Associations of Pulmonary Parameters with Accelerometer Data Focusing on Cystic Fibrosis and COPD", 3facutly of Science and Technology, Department of Computer Science, Nov. 30, 2013 (Nov. 30, 2013), XP055143921, URL:http://munin.uit.n0/bitstream/handle/l0037/6378/thesi s.pdf?sequence=4[retrieved on Oct. 1, 2014.

Kurcalte I. et al., "Circadian Heart Rate Variability in Permanent Atrial Fibrillation Patients", Electrocardiology 2014—Proceedings of the 41st International Congress on Electrocardiology, Jun. 7, 2014 (Jun. 7, 2014), XP055147062, URL: http://www.measurement,sk/1CE2014/proceedings/161.pdf [retrieved on Oct. 16, 2014].

Rabe, Klaus F. et al., "Seasonal Distribution of COPD Exacerbations in the Prevention of Exacerbations with Tiotropium in COPD Trial", Chest, Mar. 2013; 143(3):711-9.

Pitta, Fabio et al., "Physical Activity and Hospitalization for Exacerbation of COPD" Chest, Mar. 2006, 129(3):536-44.

Pitta, Fabio et al., "Characteristics of Physical Activities in Daily Life in Chronic Obstructive Pulmonary Disease", , American Journal of Respiratory and Critical Care Medicine, May 1, 2005;171(9):972-7.

Garcia-Aymerich, Judith et al., "Physical Activity and Clinical and Functional Status in COPD", Chest, Jul. 2009; 136(1):62-70.

Nunes, Deuzilane M. et al., "Actigraphic Assessment of Sleep in Chronic Obstructive Pulmonary Disease", Sleep Breath, Feb. 2012, 17(1):125-32.

Bronshtein I.N. et al., "Handbook of Mathematics", Springer; 5th edition, 2007.

Long, Xi et al., "Sinlge-Accelerometer-Based Daily Physical Activity Classification", 31st Annual International Conference of the IEEE EMBS, Minneapolis, Minnesota, USA, Sep. 2-6, 2009, pp. 6107-6110.

* cited by examiner

APPARATUS, SYSTEM, METHOD AND COMPUTER PROGRAM FOR ASSESSING THE RISK OF AN EXACERBATION AND/OR HOSPITALIZATION

CROSS-REFERENCE TO RELATED APPLICATIONS

This patent application claims the priority benefit under 35 U.S.C. § 371 of international patent application no. PCT/EP2015/064488, filed Jun. 26, 2015, which claims the benefit of international patent application no. PCT/CN2014/080981, filed Jun. 27, 2014, which claims the benefit of European Application No. EP14179997.3 filed August 6, and European Application No. EP14179993.2 filed Aug. 6, 2014, and European Application No. EP14180307.2 filed Aug. 8, 2014. These applications are hereby incorporated by reference herein.

FIELD OF THE INVENTION

The invention relates to an apparatus for assessing the risk of an exacerbation and/or hospitalization of a subject, a system for assessing the risk of an exacerbation and/or hospitalization of a subject, to a method for assessing the risk of an exacerbation and/or hospitalization of a subject, and to a computer program for assessing the risk of an exacerbation and/or hospitalization of a subject.

BACKGROUND OF THE INVENTION

Chronic obstructive pulmonary disease (COPD) is a progressive and irreversible disease which is under-diagnosed, life-threatening and mainly interferes with normal breathing. Individuals who suffer from COPD experience an intense shortness of breath during exercise, which causes a general disability. Daily activities, such as walking can become very difficult due to breathlessness as the condition gradually worsens.

COPD is a respiratory disease that is characterized by inflammation of the airways. COPD is characterized by an airflow limitation that is not fully reversible. The airflow limitation is both progressive and associated with an abnormal inflammatory response of the lungs to noxious particles or gases. Symptoms of COPD may include coughing, wheezing and the production of mucus, and the degree of severity may, in part, be viewed in terms of the volume and color of secretions.

COPD patients can be very prone to lung infections and pneumonia, which can cause a downward spiral of repeated lung infections and a further decline of lung function. Acute exacerbations of COPD have a negative impact on the health related quality of life, pulmonary function and survival of patients with COPD.

Exacerbations are the worsening of COPD symptoms. The exacerbations may be associated with a variable degree of physiological deterioration. The exacerbations may be measured as a decrease in Forced Expiratory Volume measured over one second ($FEV_1$). The exacerbations may be characterized by increased coughing, dyspnea (i.e., shortness of breath) and production of sputum. The major symptom of an exacerbation is the worsening of dyspnea (i.e., shortness of breath) while the main reaction is a lack of energy, which in turn may translate to a reduction in physical activity levels.

The exacerbations are normally caused by viral or bacterial infections and often may lead to hospitalization of the COPD patients. The frequency of exacerbations increases during the winter months due to cold stresses on the patient's body as disclosed in the article "Seasonal distribution of COPD exacerbations in the Prevention of Exacerbations with Tiotropium in COPD trial" by Rabe et al., 2013 March; 143(3):711-9. This may be due to a combination of a) the cooling of facial skin and airways, resulting in bronchoconstriction, and b) the thermoregulatory system becoming less effective with age, thus making COPD patients more susceptible for respiratory infections. The exacerbations not only limit the performance of daily activities, but also significantly decrease the health related quality of life of COPD patients. A high frequency of exacerbations is linked to a poor prognosis for survival. Also, the exacerbations often may result in hospitalization, which is the main determinant of the overall healthcare expenditure for COPD patients.

Because of the damage done when an exacerbation takes place it is desirable to predict the likely onset of an exacerbation and initiate treatments which either prevent the occurring exacerbation and/or treat the symptoms at an early stage thereby reducing the severity and damage caused by the exacerbation. Moreover, reducing and most importantly preventing exacerbations may help COPD patients lead an improved quality of life and may lower the healthcare costs for COPD patients.

To improve quality of COPD patients' lives and reduce healthcare costs by timely treating exacerbations, technologies are requested that reliably enable risk stratification of COPD patients at discharge from the hospital, monitor and support COPD patients' conditions at home, reduce hospital admissions, detect deterioration and reduce early mortality.

Clinically, the diagnosis and disease severity of COPD patients is based on the assessment of spirometric parameters; however, spirometry can be difficult to execute correctly due to patients' inability to perform forced maneuvers. Moreover there is general belief in the medical community that these parameters are insensitive to changes over short periods of time in patients with COPD, so that they may not be a reliable metric for acute respiratory events.

Up to now, no monitoring services are available that enable to assess patients' deterioration due to an exacerbation and/or risk of re-admission and indicate to clinicians, caregivers or family members a risk of an exacerbation and/or readmission of the patient.

Change of activity, in particular, a change in the intensity of a physical activity, is often mentioned as a good measure to detect exacerbations in COPD. So far, numerous approaches have been considered when studying the physical activities of COPD patients, see the article "Physical activity and hospitalization for exacerbation of COPD" by Pitta et al., Chest. 2006 March; 129(3):536-44, the article "Characteristics of physical activities in daily life in chronic obstructive pulmonary disease" by Pitta et al., Am J Respir Crit Care Med. 2005 May 1; 171(9):972-7. Epub 2005 Jan. 21, and the article "Physical activity and clinical and functional status in COPD" by Garcia-Aymerich et al., Chest. 2009 July; 136(1):62-70. doi: 10.1378/chest.08-2532. Epub 2009 Mar. 2. For example, different types of activity (such as, e.g., walking, standing, sitting, running) performed by patients have been actively studied by many researchers. Further, counting the number of steps experienced by the patient has also been looked into. All these approaches however only examine the activity of patients during their active period, such as, e.g., during day time. The symptoms of COPD do not stop when patients go to bed, of course. In many occasions, COPD patients cannot enjoy a good night sleep because of their symptoms (such as, e.g., coughing). Nonetheless, the existing studies mentioned above do not continuously study patients' activity during sleep in the home environment, i.e., during bed time in relation with hospital readmissions. The article "Actigraphic assessment of sleep in chronic obstructive pulmonary disease" by Nunes et al., Sleep Breath, 2013 March; 17(1):125-32, studies twenty-six moderate to very severe COPD patients and fifteen controls by actigraphy for at least five days. COPD patients showed increased sleep latency, mean activity, and reduced total sleep time as compared to the controls.

Various questionnaires have been used in detecting an exacerbation, however disadvantages of this method is that they are highly subjective, rely on memory recall, and must be short to ensure compliance. This can affect the sensitivity of the algorithm in detecting the onset of an exacerbation.

US 2014/012099 A1 discloses an apparatus and methods including sensing at least one parameter of a subject while the subject sleeps. The parameter is analyzed, and a condition of the subject is determined at least in part responsively to the analysis. The subject is alerted to the condition only after the subject awakes. Other applications are also described.

US 2013/310699 A1 discloses a method of monitoring a patient which includes measuring neural respiratory drive using a monitoring device, repeating the measurement either continuously or at regular time intervals, and comparing the measurements obtained in order to predict treatment failure and/clinical deterioration and/or re-admission. The neural respiratory drive is measured by obtaining a measure of the second intercostal space parasternal electromyogram. A monitoring device includes a signal input, a processing unit, and an output unit, and is arranged to measure the neural respiratory drive, store the measured value and compare it to a previously measured value for the neural respiratory drive.

WO 97/12546 A1 discloses a method and an apparatus for assessing cardiovascular risk. The method for assessing risk of an adverse clinical event includes detecting a physiologic signal in the subject and determining from the physiologic signal a sequence of intervals corresponding to time intervals between heart beats. The long-time structure of fluctuations in the intervals over a time period of more than fifteen minutes is analyzed to assess risk of an adverse clinical event. In a preferred embodiment, the physiologic signal is an electrocardiogram and the time period is at least fifteen minutes. A preferred method for analyzing the long-time structure variability in the intervals includes computing the power spectrum and fitting the power spectrum to a power law dependence on frequency over a selected frequency range such as $10^{-4}$ to $10^{-2}$ Hz. Characteristics of the long-time structure fluctuations in the intervals is used to assess risk of an adverse clinical event.

A method and apparatus for the detection of the onset of hypoglycaemia is described in AU 2012 350348 A1. A portable sensor worn by a subject is used to detect a physiological tremor signal. The tremor signal is analyzed over a period of time, and an alarm is generated when a change in the physiological tremor signal indicative of the onset of hypoglycaemia in the subject is detected. A patient or carer can then perform appropriate action, such as performing a finger prick test to determine blood sugar test and treating as required. The portable sensor can be used to detect a tremor signal indicative of the, the onset of hypoglycaemia such as a signal corresponding to a decrease in blood glucose level (BGL) below 5 mmol/l. The portable sensor can use an accelerometer and may be worn on a limb, such as an arm or leg. The sensor can be used to measure the power of the tremor signal and detect a change, such as an increase in power over time and/or an increase in the rate of change of power over time. Filtering the signal may include filtering signals outside of the range 0-50 Hz, or more specifically 7-15 Hz.

US 2010/0010552 A1 describes a method and a system for temperature analysis to provide an early marker of congestive heart failure progress that precedes a patient's symptoms. The temperature of a patient is a significant predictor of death in heart failure patients. Temperature provides a window into the physiology of the patient's underlying condition and may be used as an early marker for CHF exacerbations. The patient's temperature is taken to form a time series of temperature values. In accordance with some embodiments, the time series of temperature values is converted to the frequency domain by, for example, a discrete Fourier Transform. The frequency domain representation then is analyzed for a marker indicative of the worsening condition of the patient. In accordance with other embodiments, the patient's time series of temperature values is analyzed for a marker using, for example, Cosinor analysis. In yet other embodiments, both the time and frequency domain temperature data is analyzed for markers of the patient's worsening medical condition.

In an observational cohort study of 169 persons with COPD, May M L, Teylan M, Westan N A, Gagnon D R, Garshick E ((2013) Daily Step Count Predicts Acute Exacerbations in a US Cohort with COPD. PLoS ONE 8(4): e60400. doi: 10.1371/journal.pone.0060400) directly assessed physical activating with the StepWatch Activity Monitor, an ankle-worn accelerometer that measures daily step count. We also assessed exercise capacity with the 6-minute walk text (6MWT) and patient-reported PA with the St. George's Respiratory Questionnaire Activity Score (SGRQ-AS) acute exacerbation (AEs). The authors conclude that lower daily step count, lower 6MWT distance, and worse SGRQ-AS predict future AEs and COPD-related hospitalizations, independent of pulmonary function and previous AE history. These results support the importance of assessing PA in patients with COPD, and provide the rationale to promote PA as part of exacerbation-prevention strategies.

An objective of "Classification of Exacerbation Episodes in Chronic Obstructive Pulmonary Disease Patients" by A. Dias et al., Methods of Information in Medicine, Schattauer GmbH, DE, vol. 53, no. 2, 11 Feb. 2014, pages 108-114, is to build computational models capable of distinguishing between normal life days from exacerbation days in COPD patients, based on physical activity measured by accelerometers. The authors recruited 58 patients suffering from COPD and measured their physical activity with accelerometers for 10 days or more, from August 2009 to March 2010. During this period the authors recorded six exacerbation episodes in the patients accounting for 37 days. They were able to analyze data from 52 patients (369 patient days) and extracted three distinct sets of features from the data one set of basic features such as average one set based on the frequency domain and the last exploring the cross in formation among sensors pairs. These were used by three machine-learning techniques (logarithmic regression, neural networks, support vector machines) to distinguish days with exacerbation events from normal days. The support vector machine classifier achieved an AUC of 90%±9, when supplied with a set of features resulting from sequential feature selection method. Neural networks achieved an AUX of 83%±16 and the logarithmic regression an AUC of 67%±15. The authors conclude that none of the individual feature sets provided robust for reasonable classification of PA recording days. The results indicate that this approach has the potential to extract useful information for, but are not robust enough for medical application of the system.

WO 2013/080109 A2 provides for a health monitoring system comprising an activity monitor. The health monitoring system further comprises a processor and a memory for storing machine readable Instructions. The Instructions cause the processor to derive activity counts from the activity data acquired by the activity monitor. The instructions further cause the processor to store the activity counts in the memory, and are associated with a time. The instructions further cause the processor to calculate at least two Statistical parameters from the activity counts, wherein the at least two Statistical parameters are descriptive of the activity counts as a function of time. The instructions further causes the processor to calculate a risk score for each of the at least two Statistical parameters. The instructions further cause the processor to calculate a total risk score using the risk score for each of the at least two Statistical parameters.

The authors of "Circadian Heart Rate Variability in Permanent Atrial Fibrillation Patients" by I. Kurcalte et al. in Electrocardiology 2014—Proceedings of the $41^{st}$ International Congress on Electrocardiology assume that it is possible to use measurements of circadian heart rate (HR) changes for mortality risk and cardiac autonomic control assessment in permanent atrial fibrillation (PAF) patients. In 327 symptomatic PAF patients (259 non-diabetic, 68 diabetic), exposed to Holter monitoring in 2007-2010, circadian HR variability and Standard Heart Rate Variability (HRV) Time domain indices were calculated and compared in patients who died or survived, and non-diabetic and diabetic patients. Patients were followed for a median period of 39 months (1-60). It was found that circadian HR indices were significantly lower in the dead as compared with alive patients ($p<0.001$); in diabetic patients as compared with those without diabetes ($p<0.01$), and in diabetic patients with approved diabetic neuropathy diagnosis ($p<0.05$). Measured HRV indices didn't show significant differences in studied patients groups. Circadian HR variability showed promising predictive value for risk assessment in PAF patients.

SUMMARY OF THE INVENTION

It is an object of the present invention to provide an improved apparatus, system, method, and computer program for predicting and assessing the risk of an exacerbation and/or hospitalization, specifically for the case of a COPD patient. In particular, it is desired to improve the existing approaches by employing improved data analysis methods.

In a first aspect of the invention, there is provided an apparatus for assessing a risk of an exacerbation and/or hospitalization of a subject, the apparatus comprising: an input unit for receiving time-dependent physical activity data for said subject, said time-dependent physical activity data being obtained by an accelerometer; an activity data transform unit configured to transform said time-dependent activity data to obtain frequency-dependent activity data, a moment determination unit that is configured to compute a moment of said frequency-dependent activity data; and a risk assessment unit that is configured to assess said risk of said exacerbation and/or hospitalization of said subject based at least on said moment, wherein said moment of said frequency-dependent activity data corresponds to an integral of said frequency-dependent activity data over all frequencies, and/or wherein said moment of said frequency-dependent activity data corresponds to an integral of said frequency-dependent activity data between a first frequency and a second frequency.

An underlying aspect of the present invention is the understanding that stable patients can maintain activity levels and may have a greater variation in the range of activity levels. Use is thus made of data on how long a patient can sustain activity at different intensities and of data on whether the patient has long periods of sustained activity or shorter bursts of activity. The present invention proposes a method for risk stratification for COPD patients that may be of risk of having an exacerbation. In particular, it is proposed to apply Fourier transforms to find the frequency components of activity patterns. By measuring activity behavior in COPD patients with this technique, it was observed that patients prior to an exacerbation had activity cycles that were low in frequency and longer in duration, and the intensity of activity in these cycles were lower than patients that were recovering well. By using Fourier transforms to convert the daily activity data from the time domain to the frequency domain, the activity signal can be represented by how much information is comprised at different frequencies of activity cycles.

Said moment of said frequency-dependent activity data corresponds to an integral of said frequency-dependent activity data over a frequency interval or over all frequencies. By computing an integral of said frequency-dependent activity data, one may determine how much activity is at a specific frequency. Notably, as explained below, computing an integral of said frequency-dependent activity data may be used to determine a center-of-gravity of said frequency-dependent activity data so that an average frequency may be determined. For instance, given a set of Fourier-transformed activity data $\tilde{P}(f)$ as a function of frequency f, a center-of-gravity may be determined by dividing the term $\int \tilde{P}(f) f df$ by the term $\int \tilde{P}(f) df$. In the context of the present embodiment, a center-of-gravity may also correspond to a center-of-mass. Additionally and/or alternatively, in the context of the present embodiment, a center-of-gravity may also correspond to an expected value.

The accelerometer used for obtaining activity data, may use, for example, sensor based electrostatic technology (e.g. MEMs or piezoelectric technology), as well as other known approaches on obtaining said data.

Herein, there is proposed a method for risk stratification for COPD patients that may be of risk of having an exacerbation and/or hospital re-admission by applying Fourier transforms to find frequency components of activity patterns. A risk score can then be derived to indicate the likelihood of an upcoming exacerbation and/or an adverse event for the patient.

The term "risk", as used herein, corresponds to the likelihood of a (potentially unpleasant) event (namely, an exacerbation and/or hospitalization) to occur and thus ranges between 0% (exacerbation and/or hospitalization can be excluded) and 100% (exacerbation and/or hospitalization is certain to occur). On the other hand, the term "onset" as used herein corresponds to the beginning of something, especially something unpleasant (such as an exacerbation, which may lead to hospitalization of the subject). "Exacerbation risk" and "exacerbation onset" are related in that detecting an onset of an exacerbation usually corresponds to a higher risk of an actual exacerbation occurring. It is noted however that the "onset", as used herein, does not refer to a likelihood, but rather to a trigger or a flag, which signals that a given criteria indicative of an increased exacerbation or hospitalization is fulfilled, with the intention of intervening to prevent or reduce the severity of the exacerbation.

Preferably, in order to be able to employ past activity data, embodiments of the present invention are configured to write to and read from a data storage. Said data storage may be part of said embodiments. In another embodiment, said data storage may be accessed via networking means such as but not limited to the internet.

In a preferred embodiment, the input unit is configured for receiving time-dependent activity data comprising at least first and second activity data; wherein said first activity data is obtained by means of the accelerometer and indicative of said subject's physical activity during at least part of an active period of time; wherein said second activity data is obtained by means of the accelerometer and indicative of said subject's physical activity during at least part of a rest period of time; wherein the risk assessment unit (840) is configured to assess said risk of said exacerbation and/or hospitalization of said subject based at least on said moment and on whether an expression involving the first activity data and/or the second activity data fulfills a predetermined relationship with respect to a predetermined activity level.

In the context of this embodiment, it is particularly desired to improve the existing approaches by considering a patient's physical activity during night as well.

COPD exacerbations have an extremely negative effect on patients. Quality of life reduces, performance of daily activities can become limited and they accelerate the progression of the disease. A high frequency of exacerbations is linked to a poor prognosis for survival.

Patients that receive prompt therapy after the onset of an exacerbation are likely to have an improvement on outcomes and recover more rapidly than those that delay reporting, thus reducing the severity of the exacerbation which potentially reduces readmission costs. Failure to report exacerbations leads has been linked to an increased risk of emergency hospitalization. To support COPD patients and improve quality of life, early identification of worsening of patient conditions through intensive home monitoring and timely treatment of exacerbations has the potential to reduce hospital admissions, slow deterioration and reduce early mortality.

Various questionnaires have been used in detecting an exacerbation, however disadvantages of this method is that they are highly subjective, rely on memory recall, and must be short to ensure compliance. This can affect the sensitivity of the algorithm in detecting the onset of an exacerbation.

Quite often, COPD patients also have poor sleeping patterns and disrupted sleep due to their symptoms especially coughing. Herein, a telehealth monitoring system and service are described, which assess a patient's risk of an acute exacerbation preferably but not limited to within the first week post-discharge. Patients categorized as having a medium or high risk of an exacerbation and/or re-admission, are critically monitored for changes in physical activity which are indicative of an onset of an exacerbation and/or risk of readmissions. If this occurs, an alert is then sent via the telehealth system to clinicians, where an intervention can be made if necessary.

Risk stratification of COPD patients after a hospital readmission is described, using physical activity data from an accelerometer. As described herein, continuous monitoring of physical activity using an accelerometer can be used to assess the risk of a patient for an upcoming exacerbation resulting in a change in medication or a hospitalization. Patients that are recovering well and are stable tend to have a less disrupted sleep and a higher awake activity as a result. This is evident within the first week post-discharge, therefore it is possible to assess whether the patients have a low, medium and high risk of an upcoming exacerbation resulting in a re-admission based on these awake-sleep parameters based on at least one week of continuous activity data.

In addition, patients with COPD that are recovering well after an exacerbation will have different behavioral patterns to those that are not. Patients whose health condition is deteriorating, are less likely to perform a range of activities, and will have a very low variation in their activity levels. Day to day tasks are performed slowly and take longer to complete, therefore activity cycles tend to be longer with a lower intensity than patients that are recovering well. The activity data can be transformed from the time to the frequency domain by the Fourier transforms and multiple activity parameters can be derived from this. There are significant changes in some of these parameters a few days before an exacerbation or readmission occurs.

The Fourier transform and awake-sleep parameters can be used in conjunction together to firstly, categorize patients into a level of risk within the first week post-discharge, and secondly generate a warning to a clinician when a patient's condition is deteriorating.

Physiological data collected in the hospital at admission and discharge can also be used together with physical activity data to evaluate a patient's level of risk of an upcoming exacerbation. Additionally, a patient's symptom data can be reported via a questionnaire on a daily basis which can be used in combination with the physical activity monitoring to assess the risk of an upcoming exacerbation.

By identifying those COPD patients that are at a higher risk of an upcoming exacerbation resulting in a readmission and when patients are deteriorating, clinicians are able to intervene and potentially prevent or reduce the severity of an exacerbation.

As explained above, a change of activity, in particular, a change in the intensity of a physical activity is often mentioned as a good measure to detect the deterioration of the subject (such as, e.g., a patient) and/or the onset of an exacerbation in COPD. The existing approaches however only examine the activity of subjects (such as, e.g., patients) during their active period, such as, e.g., during day time. The symptoms of COPD do not stop when patients go to bed, of course. In many occasions, COPD patients cannot enjoy a good night sleep because of their symptoms (such as, e.g., coughing). Herein, it is proposed to use a patients' physical activity during both active (such as, e.g., day time) as well as rest (such as, e.g., sleep) time periods. A proposed system may comprise a device, which is worn or carried by the patient so as to continuously measure physical activity data. Alternatively, the system may comprise a physical activity measurement unit, such as, e.g., an accelerometer, which is worn, e.g. on the patient's wrist, and which is in communication with a risk assessment unit, which may be comprised in a personal computer or the like. The risk assessment unit may be embodied by a computer program product causing a processor to analyze the physical activity data gathered from the patient during active and rest periods. It is observed that unstable COPD patients (i.e., patients with an increased risk of readmission within the monitoring period, e.g., one month post discharge) exhibit increased activity during sleep (e.g., because they are kept awake by symptoms such as, e.g., their cough) and a decreased activity during awake hours (e.g., because they are tired and exhausted from not having had a good night of sleep). A combination of physical activity data gathered during active time periods with physical activity data gathered during rest time periods may thus be used beneficially to provide an improved risk stratification for hospitalization based, e.g., on a change in daily activity and sleep of COPD patients.

According to an embodiment, the first activity data corresponds to average activity data of said subject (e.g., a patient) during at least part of the active period; and/or the second activity data corresponds to average activity of said subject (e.g., a patient) during at least part of the rest period. By considering average activity data, the apparatus is more robust with regard to fluctuations, because only average activity data is considered. It shall be understood that the apparatus may alternatively and/or additionally consider a median of activity data. Further, it shall be understood that the average and/or the median may be determined after discarding the highest and lowest activity data measurements in order to be more robust against single outliers.

According to a further embodiment, the first activity data corresponds to average activity data of said subject (e.g., a patient) during the entire active period; and/or the second activity data corresponds to average activity of said subject (e.g., a patient) during the entire rest period. By considering average activity over an entire active and/or rest period, the preferred embodiment is more robust with regard to fluctuations, which are limited to brief time periods.

According to a further embodiment, the apparatus is configured to compare the first activity data to a first activity level; and/or the apparatus is configured to compare the second activity data to a second activity level. Comparing activity data to activity levels (such as, e.g., thresholds, upper limits, and/or lower limits) advantageously addresses the fact that a typical patient exhibits different average activity levels during active and rest periods. Namely, even for a healthy person, activity data during a rest period will be low. Differentiating between active and rest periods thus involves the advantage that low activity during rest periods is not misinterpreted as an overall low activity (which would potentially be interpreted as an increased readmission risk).

According to a further embodiment, the first activity level is higher than the second activity level. The preferred embodiment thus takes into account that an average activity level during an active period is usually higher than an average activity level during rest period.

According to a further embodiment, the predetermined relationship comprises the conditions that (1) the first activity data is smaller than the first activity level, and (2) the second activity data is higher than the second activity level. Typically, as explained in more detail herein below, an unstable COPD patient is more restless at night (i.e., exhibiting higher activity data during the rest period), but tired during the day (i.e., exhibiting less activity data during the active period). In contrast, a stable COPD patient with a lower risk of readmission within the monitoring period, e.g., one month post discharge, typically exhibits less movement during sleep (i.e., less activity during rest period), and is more active during the day (i.e., increased activity during active period).

According to a further embodiment, the apparatus is configured to compare the first activity data to past first activity data, wherein the past first activity data correspond to first activity data gathered on one or more previous days; and/or the apparatus is configured to compare second activity data to past second activity data, wherein the past second activity data correspond to second activity data gathered on the one or more previous days. By comparing the patient's activity data for a given day to the patient's activity data of the previous day(s), the preferred embodiment enables the monitoring of a time evolution of the COPD patient's activity. Preferably, in order to be able to employ past first and second activity data, a system in accordance with the present invention is configured to write to and read from a data storage. Said data storage may be part of said system. In another embodiment, said data storage may be accessed via networking means such as but not limited to the internet.

According to a further embodiment, the predetermined relationship comprises the conditions that (1) the first activity data is lower in comparison to first activity data when not at risk and (2) the second activity is higher in comparison to first activity data when not at risk. As explained in more detail herein below, an increased activity level during rest periods and a decreased activity level during active periods may typically indicate an increased risk for an exacerbation or hospital readmission during the monitoring period.

According to a further embodiment, the predetermined relationship comprises the conditions that (1) the first activity data is smaller than one or more of past first activities, and (2) the second activity is higher than one or more of past second activities. As explained in more detail herein below, an increased activity level during rest periods and a decreased activity level during active periods may typically indicate an increased risk for an exacerbation or hospital readmission during the monitoring period.

According to a further embodiment, the apparatus is configured to determine a ratio between first activity data and second activity data. By considering ratios, the preferred embodiment achieves a reduced dependency on the physical activity measurement unit (e.g., accelerometer) used. This is because the absolute values of physical activities are ignored in favor of a ratio of first and second activity data. Put differently, a first accelerometer may yield very high absolute values of activity data (e.g., because the first accelerometer is very sensitive), whereas a second accelerometer may yield very low absolute values of activity data (e.g., because the second accelerometer is less sensitive). In this case, comparing the absolute values to predetermined thresholds will lead to a different result, depending on the accelerometer used. Considering ratios of activity data however is less prone to specific details of the accelerometer, as long as the accelerometer output is approximately proportional to the patient's physical activity. Preferably, the total daily awake activity counts and the total daily sleep activity counts are acquired, and their ratio is computed. This way, the duration of active and rest periods is taken into account. Alternatively and/or additionally, the daily mean awake activity counts and the daily mean sleep activity counts are determined, and their ratio is computed.

According to a further embodiment, the apparatus is configured to compare the ratio to a ratio activity level. For instance, the ratio activity level may correspond to an average activity level of a patient group. For instance, if the ratio is equal to or larger than the average activity level of a group of stable COPD patients who have a lower risk of having an exacerbation or readmission during the monitoring period (i.e., for instance, first activity data is high and second activity data is low), the risk of an exacerbation and/or hospitalization is low. On the other hand, if the ratio is smaller than the average activity level of a group of unstable COPD patients (i.e., for instance, first activity data is low and second activity data is high), the risk of an exacerbation and/or hospitalization may be high.

According to a further embodiment, the predetermined relationship comprises the condition that the ratio is smaller than the ratio activity level. This preferred embodiment makes use of the fact that if the ratio is smaller than the average activity level of a group of unstable COPD patients (i.e., for instance, first activity data is low and second activity data is high), the risk of an exacerbation and/or hospitalization may be high.

According to a further embodiment, the apparatus is configured to compare the ratio to past ratios, wherein the past ratios correspond to ratios between first activity data and second activity data gathered on one or more previous days. By comparing the measured ratio for a given day to the measured ratio of the previous day(s), the preferred embodiment enables monitoring of a time evolution of the COPD patient's activity.

According to a further embodiment, the apparatus is configured to determine a difference between first activity data and second activity data. According to a further preferred embodiment, the apparatus is configured to compare the difference to a difference activity level. The difference activity level may correspond to, e.g., a threshold. According to a further preferred embodiment, the predetermined relationship comprises the condition that the difference is lower than the difference activity level.

According to a further embodiment, the predetermined relationship comprises the condition that the ratio is smaller than one or more of past ratios. Typically, an increased activity level during rest periods and a decreased activity level during active periods may indicate an increased risk for hospital readmission. Accordingly, a decreased ratio (i.e., activity data during rest period high and activity data during active periods low) may indicate an increased risk of an exacerbation or hospital readmission. Continuous low ratios can indicate an increased risk of an exacerbation or hospital readmission. Note that one day with a low ratio might not necessarily mean increased risk of an exacerbation. However, if a continuously low ratio persists over some days this would be an indication for an increased risk of an exacerbation and/or hospital re-admission.

According to a further embodiment, the apparatus is configured to determine a difference between first activity data and second activity data. Stable COPD patients who have a lower risk of having an exacerbation or readmission during the monitoring period have a high value for the difference between the activity level during active periods minus the activity level during the rest periods. With a low activity level during the rest period in these patients, this difference can be close to the activity level during active periods. Unstable COPD patients who have a higher risk of having an exacerbation or readmission during the monitoring period have a much lower value for the difference between the activity level during active periods minus activity level during the rest periods, e.g., the first activity data is low compared to stable situation and the second activity data is high compared to stable situation, resulting in a smaller difference.

According to a further embodiment, the apparatus is configured to divide a difference between daily awake activity count and sleep activity count by the total daily activity count.

According to a further embodiment, the apparatus is configured to determine the fraction of daily activity count occurring during sleep by dividing the sleep activity count by the total daily activity count. That is, if 40% of the total daily activity count is contributed from activity counts measured during sleep of the subject, the fraction of daily activity count occurring during sleep corresponds to 0.4.

According to a further embodiment, the apparatus further comprises an alarm configured to generate an alarm indication to the patient and/or to the patient's physician or caretaker, when the predetermined relationship is satisfied. Preferably, the alarm may notify the patient, when an increased exacerbation and/or readmission risk occurs. Alternatively and/or additionally, the alarm may notify the physician or caretaker directly.

According to a further embodiment, the physical activity measurement unit comprises an accelerometer, in particular in the form of a piezoelectric sensor.

In a further preferred embodiment, said risk assessment unit is configured to identify an increased risk of said exacerbation and/or hospitalization of said subject if a moment for said subject corresponding to activity data gathered on a first day is greater than a moment for said subject corresponding to activity data gathered on a second day, said first day being prior to said second day. By configuring the risk assessment unit such that an increased risk of said exacerbation and/or hospitalization is detected when the computed moment decreases from one day to another day (which may be the subsequent day, but which may also be a day which is several days after the first day), the preferred embodiment takes into account that an exacerbation is more likely to occur when the patient's moment decreases. The decrease of the patient's moment corresponds to activity cycles lower in frequency and intensity, so the patient is unable to maintain activity levels of higher intensities anymore, which may be indicative of an increased risk of an exacerbation and/or hospitalization.

In a further preferred embodiment, said risk assessment unit is configured to compare a first moment to a second moment, where said first moment corresponds to activity data gathered during a first time period on a first day, where said second moment corresponds to activity data gathered during a second time period on a second day. By configuring the risk assessment unit such that activity data from different days are compared, the preferred embodiment takes into account that an exacerbation and/or hospital re-admission is more likely to occur when the patient's moment decreases. The decrease of the patient's moment corresponds to activity cycles lower in frequency and intensity so the patient is unable to maintain activity levels of higher intensities anymore, which may be indicative of an increased risk of an exacerbation and/or hospitalization.

In a further preferred embodiment, said risk assessment unit is configured to assess said risk of said exacerbation and/or hospitalization of said subject based on a moment gradient. By configuring the risk assessment unit such that moment gradients are taken into account, the day-to-day change of a patient's moment may be taken into account. That way, if a moment decreases from one day to another (negative gradient), but increases again on the subsequent day (positive gradient), the patient may be classified at lower risk than a patient where the moment decreases from one day to another (negative gradient), and decreases further on the subsequent day (negative gradient). Such a patient (with two or more subsequent negative gradients) may be more likely to exhibit an exacerbation so that the according risk would be assessed to be higher.

In a further preferred embodiment, said moment gradient corresponds to a change in moment for said subject from a first day to a second day, said first day being prior to said second day. As explained, by configuring the risk assessment unit such that moment gradients are taken into account, the day-to-day change of a patient's moment may be taken into account. It has to be noted however that the terms "first" and "second" only serve to distinguish one day from another. These terms do not necessarily imply that the "second" day is the very next day to the "first" day. Instead, the second day may be any day after the first day, such as, e.g., two days later, three days later, four days later, etc.

In a further preferred embodiment, said moment of said frequency-dependent activity data corresponds to an integral of said frequency-dependent activity data between a first frequency and a second frequency. By computing an integral of said frequency-dependent activity data for specific frequency ranges, one may consider physical activity cycles of corresponding durations. That is, by determining the amount (i.e., the integrated power) of activity cycles lasting between a first time and a second time (e.g., between 30 and 60 minutes), one may assess the quantity and intensity of activity cycles of said time duration.

In a further preferred embodiment, said first frequency corresponds to an activity cycle of 120 minutes and wherein said second frequency corresponds to an activity cycle of 60 minutes and/or wherein said first frequency corresponds to an activity cycle of 90 minutes and wherein said second frequency corresponds to an activity cycle of 60 minutes and/or wherein said first frequency corresponds to an activity cycle of 60 minutes and wherein said second frequency corresponds to an activity cycle of 30 minutes and/or wherein said first frequency corresponds to an activity cycle of 30 minutes and wherein said second frequency corresponds to an activity cycle of 15 minutes. The above-mentioned time intervals have been found to be good indicators of how well a subject recovers. This is even more so, when considering the day-to-day evolution of the respective moments.

In a further preferred embodiment, said moment of said frequency-dependent activity data corresponds to a center-of-gravity of said frequency-dependent activity data. By computing a center-of-gravity of said frequency-dependent activity data, the preferred embodiment proposes to identify the mean duration of physical activity cycles. Said mean duration of physical activity cycles will correspond to the inverse of the determined center-of-gravity of the power spectrum for said frequency-dependent activity data.

In a further preferred embodiment, said time-dependent activity data corresponds to activity data as a function of time gathered during a first time period.

In a further preferred embodiment, said activity data transform unit is configured to Fourier-transform said time-dependent activity data to frequency-dependent activity data. The Fourier transform is a mathematical transformation well known to the skilled person, which can be used to transform signals in the time domain to the frequency domain (and vice versa). Details and examples on Fourier transforms may be found, e.g., in the book "Handbook of Mathematics", Springer; 5th ed. 2007, by I. N. Bronshtein et al. As explained above, by using Fourier transforms to convert the daily activity data from the time domain to the frequency domain, the activity signal can be represented by how much information is comprised at different frequencies of activity cycles.

In a further preferred embodiment, said apparatus is configured to indicate to a user whether said risk of an exacerbation and/or hospitalization is above a predetermined threshold. By indicating to a user whether said risk of an exacerbation and/or hospitalization is above a predetermined threshold, the user may be warned that an exacerbation and/or hospitalization is likely to occur. The user may be the subject or a physician. A simple traffic light warning system may be used to provide a warning indication to the patient or to the clinician in view of the symptoms of the patient. This information can then be used to classify whether the patient is at risk for an exacerbation and/or hospitalization. For instance, a patient whose daily moment stays roughly the same or increases over time may be classified stable. In fact, even a variation over days might be acceptable, as long as the overall trend is stable or increasing. On the other hand, a patient whose daily moment decreases over time may be classified unstable. For patients classified as unstable, there is an increased risk of hospital readmission so that a warning indication may be issued to the patient or to the clinician. Preferably, each day's classification is logged in a database and/or communicated to the patient's physician for review. Communication to the patient's physician may be performed via the internet, an automatic telephone message, or via a SMS. Based on the classification result, the physician may decide to contact the patient for a check-up procedure. Preferably, based on the classification result, the physician may decide to intervene to prevent or reduce the severity of the exacerbation.

In a second aspect of the present invention, there is provided a system for assessing a risk of an exacerbation and/or hospitalization of a subject, the system comprising: a physical activity measurement unit that is configured to gather time-dependent physical activity data for said subject by means of an accelerometer; and an apparatus in accordance with the first aspect of the present invention; wherein said input unit of said apparatus is configured to receive said time-dependent activity data from said physical activity measurement unit.

In a further preferred embodiment, said system comprises a storage unit configured to store said time-dependent activity data.

In a third aspect of the present invention, there is provided a method for assessing a risk of an exacerbation and/or hospitalization of a subject, the method comprising: receiving time-dependent physical activity data for said subject obtained by an accelerometer; transforming said time-dependent activity data to obtain frequency-dependent activity data, computing a moment of said frequency-dependent activity data; and assessing said risk of said exacerbation and/or hospitalization of said subject based at least on said moment, wherein said moment of said frequency-dependent activity data corresponds to an integral of said frequency-dependent activity data over all frequencies, and/or wherein said moment of said frequency-dependent activity data corresponds to an integral of said frequency-dependent activity data between a first frequency and a second frequency.

In a fourth aspect of the present invention, there is provided a computer program for assessing a risk of an exacerbation and/or hospitalization of a subject, the computer program comprising program code means for causing an apparatus for assessing the risk of an exacerbation and/or hospitalization as defined in the first aspect to carry out the steps of the method for assessing the risk of an exacerbation and/or hospitalization as defined in third aspect, when the computer program is run on a computer controlling the apparatus for assessing the risk of an exacerbation and/or hospitalization.

In a fifth aspect, physiological data such as BMI, age, spirometry, history of exacerbation, is collected in the hospital at admission and discharge. It can also be used together with physical activity data to determine a patient's level of risk of an upcoming exacerbation and/or hospitalization. A similar monitoring system as in the first aspect may be used.

In a sixth aspect, patient's symptom data can be collected via a questionnaire on a daily basis. Examples of symptoms include breathlessness, coughing, sputum production and sputum color, which in combination with the physical activity monitoring, can be used to assess the risk of an upcoming exacerbation. A similar monitoring system as described with reference to the first aspect may be used.

It shall be understood that the apparatus of claim 1, the system of claim 13, the method of claim 14 and the computer program product of claim 15 have similar and/or identical preferred embodiments as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
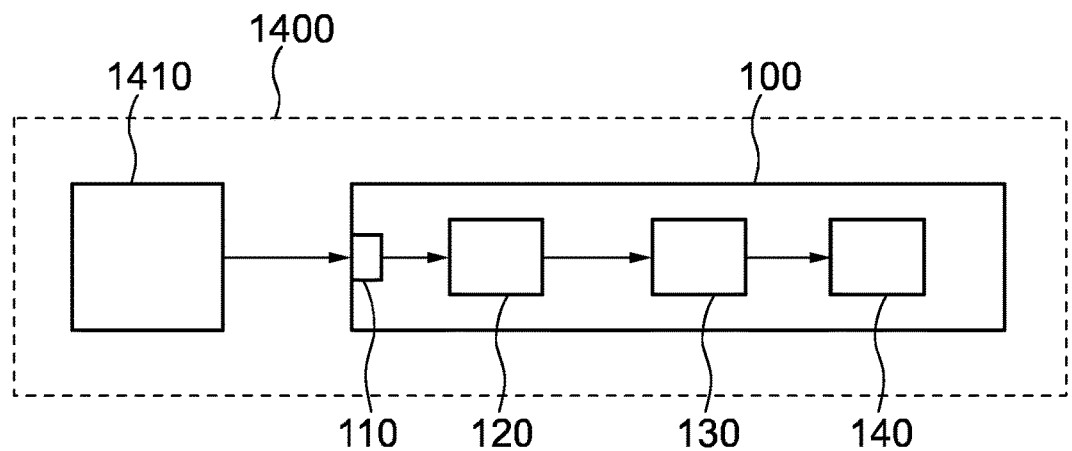
FIG. 1 shows schematically and exemplarily an embodiment of a system for assessing a risk of an exacerbation and/or hospitalization of a subject.

FIG. 1 shows schematically and exemplarily an embodiment of a system 1400 for assessing a risk of an exacerbation and/or hospitalization of a subject. System 1400 comprises a physical activity measurement unit 1410 that is configured to gather time-dependent activity data for said subject. System 1400 further comprises an apparatus 100 for assessing a risk of an exacerbation and/or hospitalization of a subject, the apparatus 100 comprising: an input unit 110 for receiving time-dependent activity data for said subject; an activity data transform unit 120 configured to transform said time-dependent activity data to obtain frequency-dependent activity data, a moment determination unit 130 that is configured to compute a moment of said frequency-dependent activity data; and a risk assessment unit 140 that is configured to assess said risk of said exacerbation and/or hospitalization of said subject based at least on said moment. Risk assessment unit 140 may however also be configured to assess said risk of said exacerbation and/or hospitalization of said subject based on a subset or all of the respective parameters described herein. Input unit 110 of apparatus 100 is configured to receive said time-dependent activity data from physical activity measurement unit 1410.

Figure 2:
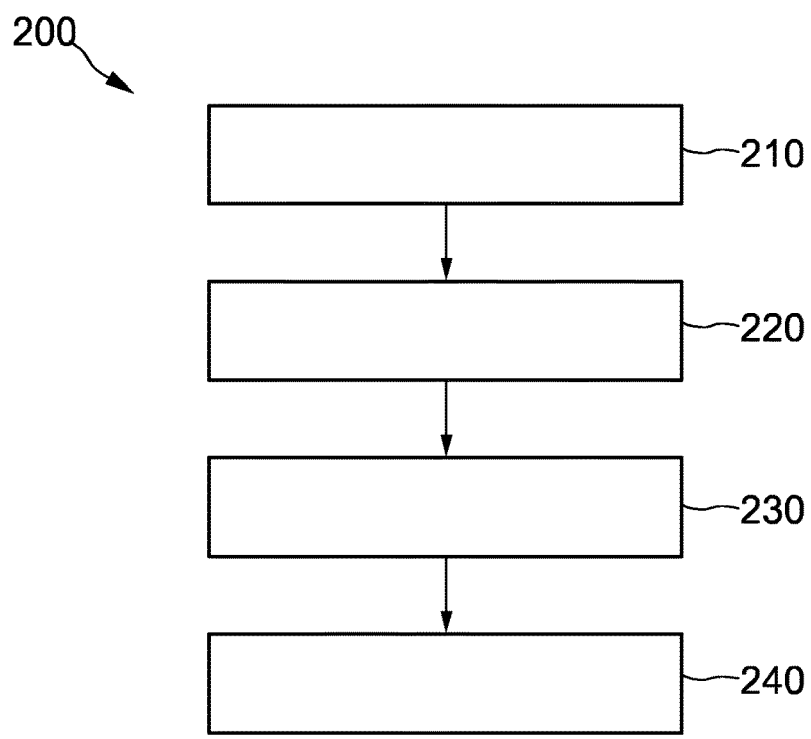
FIG. 2 shows schematically and exemplarily an embodiment of a method for assessing a risk of an exacerbation and/or hospitalization of a subject.

FIG. 2 shows schematically and exemplarily an embodiment of a method 200 for assessing a risk of an exacerbation and/or hospitalization of a subject. In a first step 210, method 200 proposes to receive time-dependent activity data for said subject. In a second step 220, method 200 proposes to transform said time-dependent activity data to obtain frequency-dependent activity data. Preferably, there is performed a Fourier-transform on said time-dependent activity data to obtain said frequency-dependent activity data. In a third step 230, method 200 proposes to compute a moment of said frequency-dependent activity data. In a fourth step 240, method 200 proposes to assess said risk of said exacerbation and/or hospitalization of said subject based on said moment.

The present invention relates to the analysis of activity data, from an accelerometer to assess the risk of a subject (i.e., a patient) for an upcoming exacerbation requiring a change in medication or hospitalization. Patients with COPD that are recovering well after an exacerbation will have different behavioral patterns to those that are not. Patients whose health condition is deteriorating are less likely to perform a range of activities, and will have a very low variation in their activity levels. Day-to-day tasks are performed slower and thus take longer to complete. Consequently, activity cycles tend to be longer with a lower intensity than for patients that are recovering well.

In a first step, the present invention proposes to apply a Fourier transform to activity data of a subject. The Fourier transform is a mathematical transformation well known to the skilled person, which can be used to transform signals in the time domain to the frequency domain (and vice versa). Details and examples on Fourier transforms may be found, e.g., in the book "Handbook of Mathematics", Springer; 5th ed. 2007, by I. N. Bronshtein et al. By using Fourier transforms to convert the daily activity data from the time domain to the frequency domain, the activity signal can be represented by how much information is comprised at different frequencies of activity cycles. To that extent, a frequency of 0.5 cycles per minute reflects an activity cycle with a duration of two minutes and the power associated with that frequency reflects the intensity of the activity carried out. Power can then be plotted against frequency represented by the power spectrum.

Figure 3:
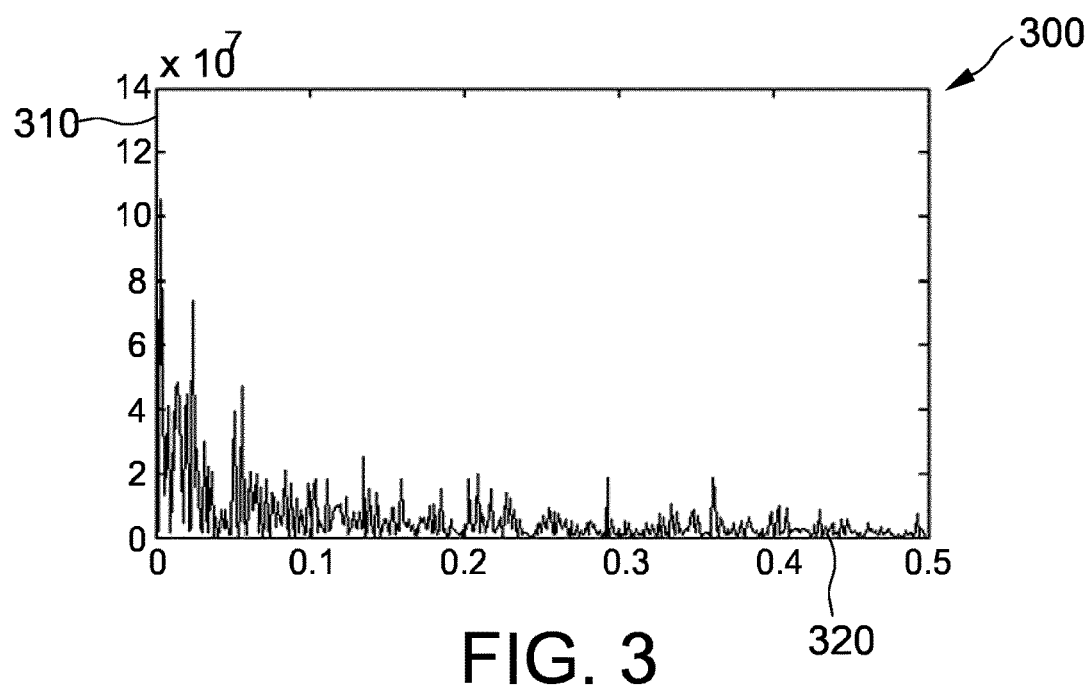
FIG. 3 shows schematically and exemplarily a power spectrum for a subject acquired during one day.

FIG. 3 shows schematically and exemplarily a power spectrum 300 for a subject acquired during one day. In particular, there is shown power 310 (in arbitrary units) over frequency 320 (in cycles per minute). Power spectrum 300 reveals how much information is comprised at a particular frequency. For instance, at a frequency 320 of approximately 0.05 cycles per minute, a power of approximately $4*10^7$ units is observed. This means that the subject underwent an activity cycle of 20 minutes. As explained above, the present invention employs information concerning how often a subject is active. That is, if a subject is active every 20 minutes, the Fourier-transformed activity data would yield a single peak at 0.05 cycles per minute. A frequency of 0.5 cycles per minute corresponds to an activity cycle of 2 minutes (i.e., the inverse of 0.5/minute). Comparing the powers of two frequencies may be used as follows: If the power is $0.2*10^7$ units for a frequency of 0.5 cycles per minute, compared to a power of $2*10^7$ units for a frequency of 0.2 cycles per minute, this indicates that a higher intensity of activity was carried out at 0.2 cycles per minute.

Power spectrum 300 (i.e., the power-vs.-frequency data) can be used to determine how much activity is at specific frequencies 320 by computing the integral of this defined as the moment. Different parameters can be derived from this, for example, the daily moment of activity cycles lasting between 30 and 60 minutes (by integrating between 0.0166 cycles per minute (i.e., the inverse of 60 minutes) and 0.0333 cycles per minute (i.e., the inverse of 30 minutes)), the daily average length of activity pattern (by computing the sum of all power values divided by the moment) and mean daily power (by adding up the power values and dividing by the number of measurements).

Figure 4:
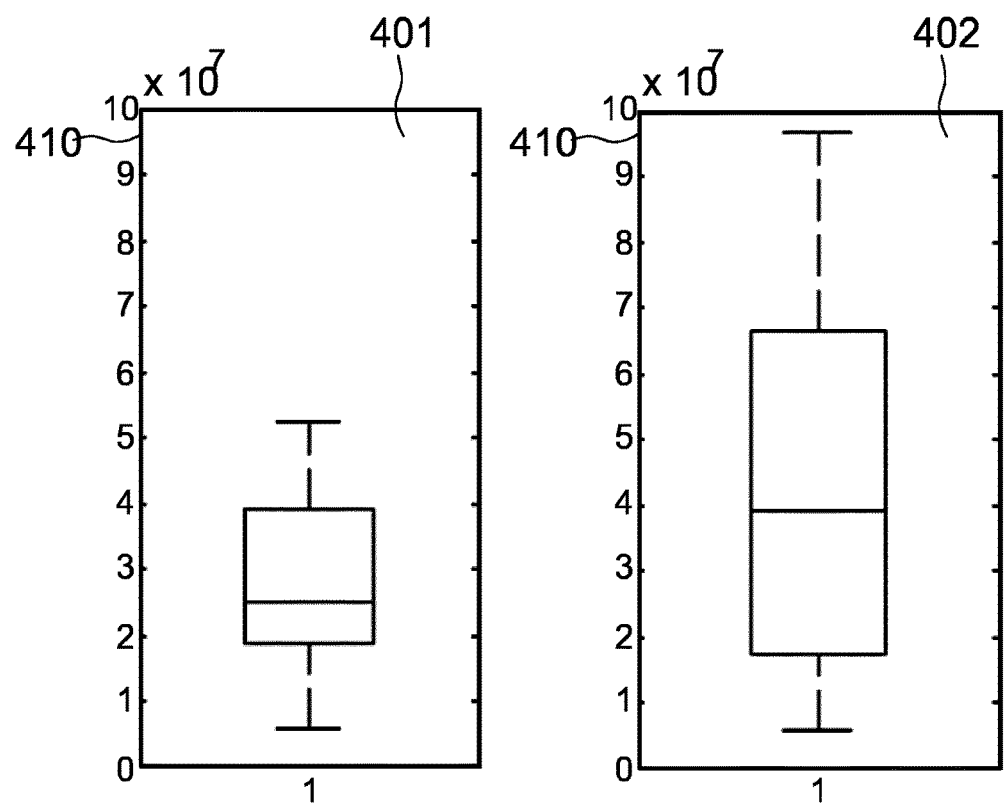
FIG. 4 shows how the daily moment of activity lasting between 30 and 60 minutes differs between COPD patients who had an exacerbation and those recovering well and did not have an exacerbation.

FIG. 4 shows how the daily moment 410 of activity cycles lasting between 30 and 60 minutes differs between COPD patients who had an exacerbation (panel 401 of FIG. 4) and those recovering well and did not have an exacerbation (panel 402 of FIG. 4). In the specific example shown in FIG. 4, the data correspond to 40 non-readmitted patients and 11 patients with a COPD readmission or exacerbation within one month post discharge. In fact, FIG. 4 shows one moment per subject the mean value over the period. Thus, for readmitted subjects the data correspond to the mean from all compliant days before readmission, and for non-readmitted subjects, the data correspond to the mean over a one month period (where the subjects had worn activity monitors). FIG. 4 is a box plot. The box indicates the interquartile range of the data, and the 'error bars' show the maximum and minimum values. The moment for patients that are recovering well is much higher in comparison to those patients that had an exacerbation. This indicates that patients that are recovering well generally have a higher moment which signifies that they have maintained greater levels of activity during activity cycles of 30 to 60 minutes.

Figure 5:
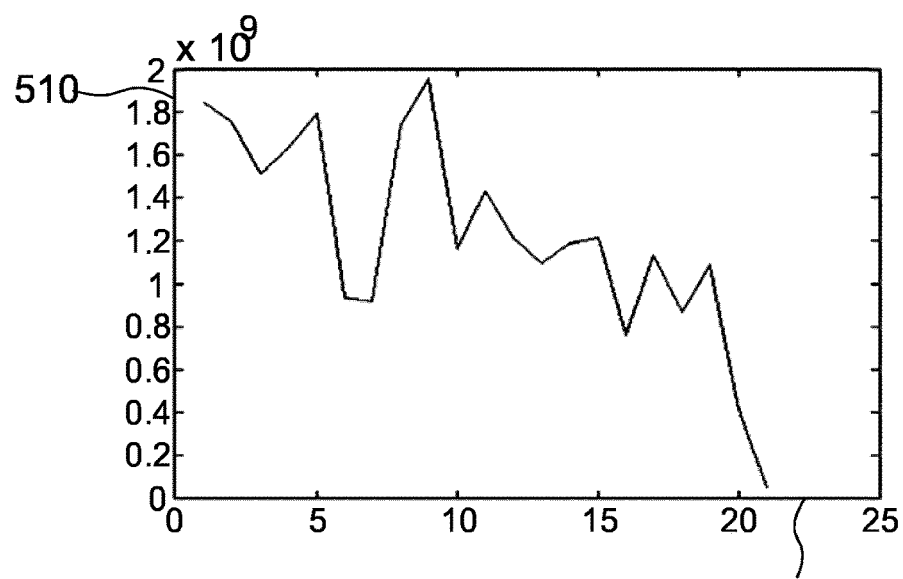
FIG. 5 shows an example of how the daily moment value changes over the course of three weeks post discharge.

FIG. 5 shows an example of how the daily moment value 510, i.e., the integrated power spectrum over all frequencies, as a function of time (axis 520 shows the number of days post discharge) changes over the course of three weeks post discharge. In the example shown, the daily moment 510 is gradually declining and the patient had a COPD readmission on day 22. This lower moment value indicates that activity cycles become longer in duration. Consequently, physical activities are performed less frequently and with a lower intensity.

Further embodiments involve the computation of awake and sleep activity counts. Further embodiments involve assessing the duration spent in low, medium, and high intensity levels. Preferably, day-to-day variations in these parameters are also determined. These parameters can be used in conjunction with the parameters derived through the Fourier transform to determine a daily risk score indicating the likelihood of an exacerbation.

A risk assessment unit in accordance with the present invention is preferably used in combination with an accelerometer as an example of, a device capable of measuring a patient's physical activity so as to determine the continuous activity behavior of the patient. Preferably, the subject's activity data is stored on a storage medium for subsequent processing. Alternatively and/or additionally, the subject's activity data may be transmitted to a database, e.g., by means of an internet or other network connection. When subsequent processing with a risk assessment unit according to the present invention is desired, the subject's activity data may be retrieved from the storage medium. Additionally and/or alternatively, the subject's activity data may be retrieved from the above-mentioned database via the above-mentioned internet or other network connection. It is further contemplated that the risk assessment unit comprises storage means for storing the subject's activity data. It is further contemplated that the physical activity measurement unit comprises storage means for storing the subject's activity data.

An algorithm in accordance with the present invention preferably uses Fourier transform methods to derive parameters which represent the patients' daily activity cycles and the amount of variation in the range of activity levels. These parameters can then be compared to the previous day or days. In general, parameters to evaluate include, but are not limited to, a moment, a mean power, an average length of the activity pattern, a coefficient of the variance of the activity count, a standard deviation power, a mean activity count, a standard deviation activity count, a moment of an activity cycle lasting more than 120 minutes, a moment of an activity cycle lasting between 60 and 120 minutes, a moment of an activity cycle lasting between 60 and 90 minutes, a moment of an activity cycle lasting between 30 and 60 minutes, a moment of an activity cycle lasting between 15 and 30 minutes, a moment of an activity cycle lasting less than 15 minutes, and a moment of an activity cycle lasting less than 10 minutes.

Combinations of these activity parameters derived using the Fourier transform along with other awake and sleep activity parameters can be used as part of a multi-parametric algorithm to determine a daily risk score which provides an indication to the patient or clinician on the condition of the patient. This information in conjunction with patient history and physiological data can then be used to classify whether the patient is at risk of an exacerbation.

Figure 6:
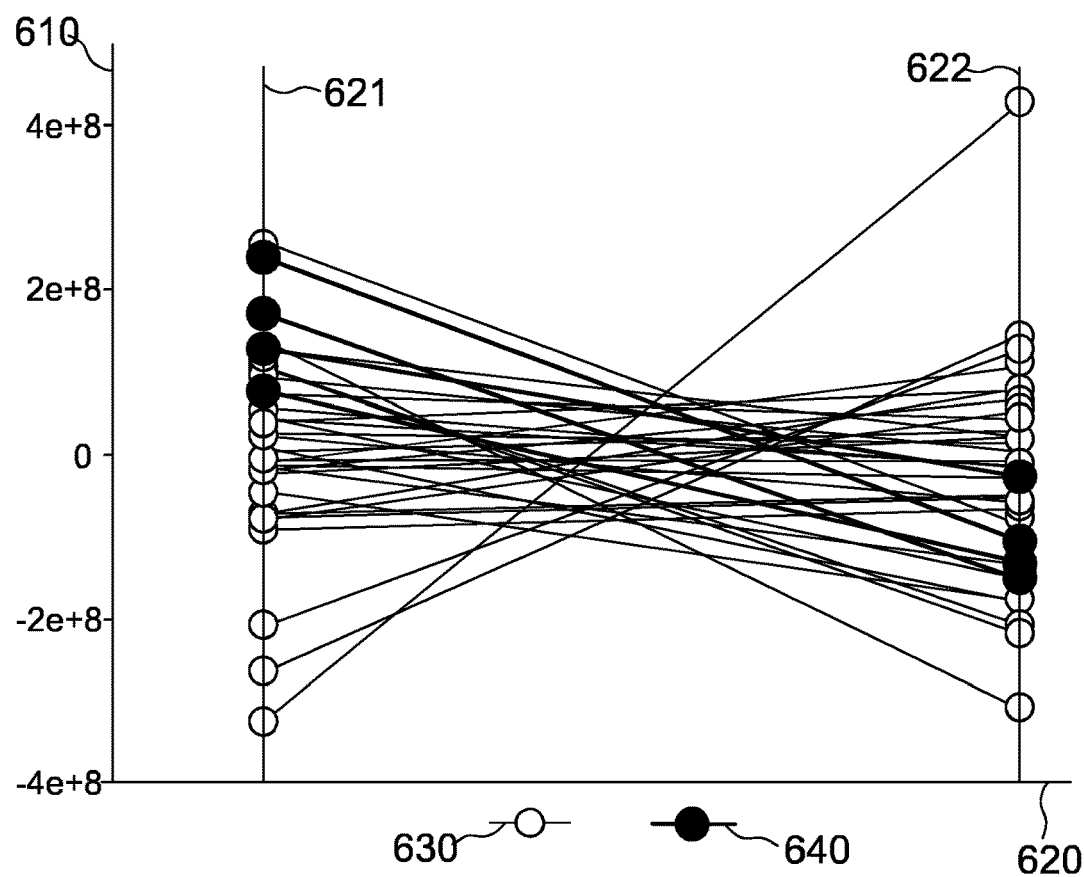
FIG. 6 shows an example of how the moment gradient varies over time.

FIG. 6 shows an example of how a moment gradient 610 varies over time (shown on axis 620). That is, the y-axis of FIG. 6 shows the change in moment and not the moment itself. A negative moment gradient means that the moment has a decreasing trend. A positive moment gradient means that the moment has an increasing trend. FIG. 6 shows that the daily moment gradient for well-recovering subjects is hardly changing (apart from a few exceptions). Thus, for these patients, a decreasing moment is no cause for alarm as long as the decrease does not "accelerate", i.e., as long as the gradient does not change as well. On the other hand, the moment gradient does change (in fact, it decreases) for patients who were readmitted. Thus, for these patients, the moment decreased faster and faster which can consequently be used to predict an increased risk of an exacerbation or readmission. Data are shown for one week post discharge (line 621) and for two weeks post discharge (line 622). Open circles 630 correspond to data for patients who were not readmitted (i.e., for patients who recovered well). Filled circles 640 correspond to data for patients who were readmitted eventually (i.e., for patients who did not recover well). On average, readmitted patients show a decline in the moment gradient over time, reflecting the lack of variation in the range of activity levels during the week prior to readmission. In contrast, there is no change in the non-readmitted patients between weeks one and two post discharge. The results in FIG. 6 show that there is a significant difference in the moment gradient between weeks one and two for readmitted patients (p=0.020). In addition, although some patients in the non-readmitted group have a similar pattern to the readmitted, there is no significant difference between weeks one and two for non-readmitted patients (p=0.350).

A simple traffic light warning system may be used to provide a warning indication to the patient or to the clinician in view of the symptoms of the patient. This information can then be used to classify whether the patient is at risk for an exacerbation and/or hospitalization. For instance, a patient whose daily moment stays roughly the same or increases over time may be classified stable. On the other hand, a patient whose daily moment decreases may be classified unstable. For patients classified as unstable, there is an increased risk of hospital readmission so that a warning indication may be issued to the patient or to the clinician. Preferably, each day's classification is logged in a database and/or communicated to the patient's physician for review. Communication to the patient's physician may be performed via the internet, an automatic telephone message, or via a SMS. Based on the classification result, the physician may decide to contact the patient for a check-up procedure. Preferably, based on the classification result, the physician may decide to intervene to prevent or reduce the severity of the exacerbation.

Figure 7:
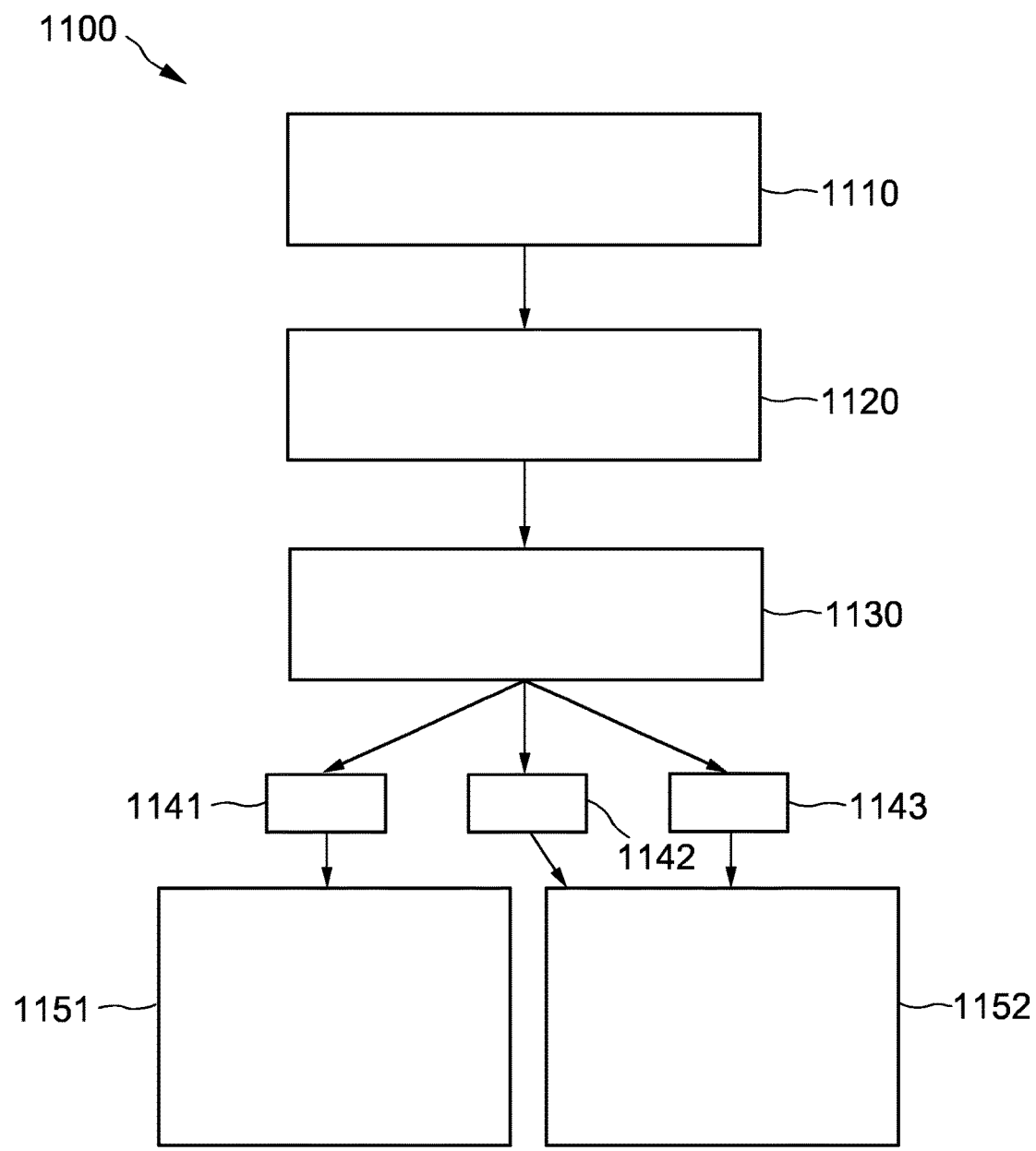
FIG. 7 illustrates the stages involved in a monitoring system implementing the present invention.

FIG. 7 illustrates a workflow 1100 involved in a monitoring system implementing an embodiment of the present invention. At stage 1110, a patient exhibiting COPD symptoms is admitted to hospital. Physiological data is collected at admission and discharge. At stage 1120, the patient is discharged from the hospital and may go back home. The patient's physical activity is preferably monitored continuously over day and night. In addition, the patient may be asked to complete a daily questionnaire to report symptoms on a daily basis. At stage 1130 which is preferably carried out within the first-week post-discharge (such as, e.g., on the fifth day post-discharge), a baseline is determined by initially categorizing the patient. Risk of an acute exacerbation resulting in a hospital re-admission may be determined based on awake-sleep activity parameters and on physiological data. Categories may involve "low risk" 1141, "medium risk" 1142, and "high risk" 1143, but lower and higher numbers of categories are conceivable, too. Next, for "low risk"-patients, it is determined whether the risk category is to be reassessed (stage 1151). Namely, stable patients recovering well typically display a strong variation in Fourier-transformed activity data and for example high ratios for awake/sleep activity. If there is a continuous lack of variation in these parameters or a steady decline, the risk category shall be reassessed. For "high risk"-patients, it is assessed whether a clinician is to be alerted (stage 1152). That is, for these patients, daily symptoms and activity parameters are critically monitored with a careful consideration of Fourier-transformed activity data and awake-sleep activity parameters. A lack of daily variation in the moment and for example low values for the awake/sleep ratio is potentially indicative of an upcoming exacerbation and/or an increased risk of hospital re-admission. Hence, a warning is sent to the clinician and an intervention may be made in order to prevent the exacerbation.

In a further embodiment, a monitoring system is described, which involves the (e.g., continuous) monitoring of physical activity post discharge to initially stratify patients into categories of risk based on activity data (e.g., within the first week post-discharge). Patients with a medium to high risk are critically monitored and an alert is sent to a clinician when changes in the Fourier transform and awake-sleep parameters are typical of an upcoming exacerbation and/or and increased risk of hospitalization.

Figure 8:
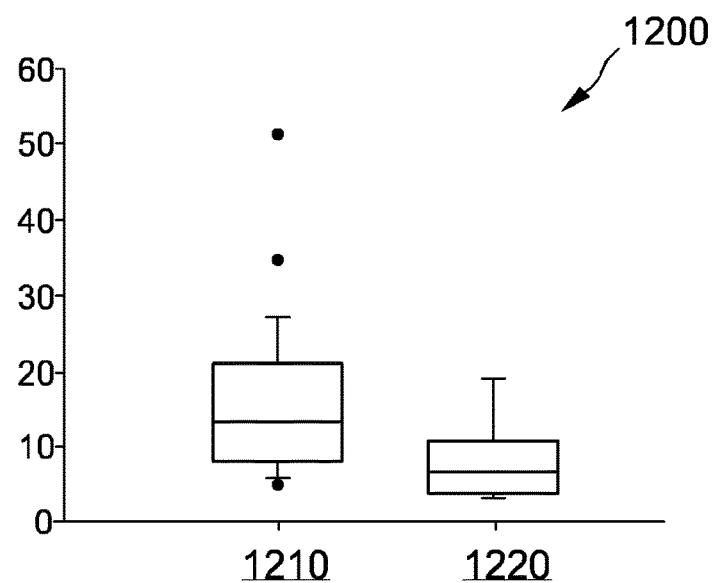
FIGS. 8 and 8a show the ratio of the mean awake activity count to mean sleep activity count in non-readmitted and readmitted patients and the corresponding ROC curve.
Figure 8A:
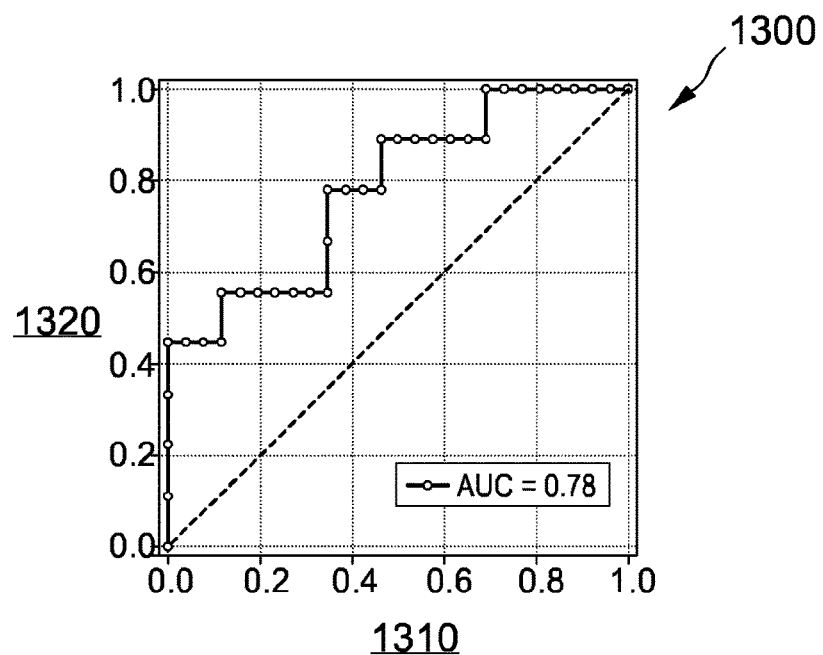

FIGS. 8 and 8a show the ratio of the mean awake activity count to mean sleep activity count 1200 for non-readmitted patients 1210 and readmitted patients 1220 in the recovery period, days one to five post-discharge, as well as the corresponding receiver operating characteristic curve 1300 (displaying sensitivity 1320 over specificity 1310 with an area under the curve AUC of 0.78). Within the first five days, the ratio is generally lower in readmitted patients. There is a significant difference in the ratio between patients readmitted within one month post-discharge and non-readmitted patients (p<0.006).

Figure 9:
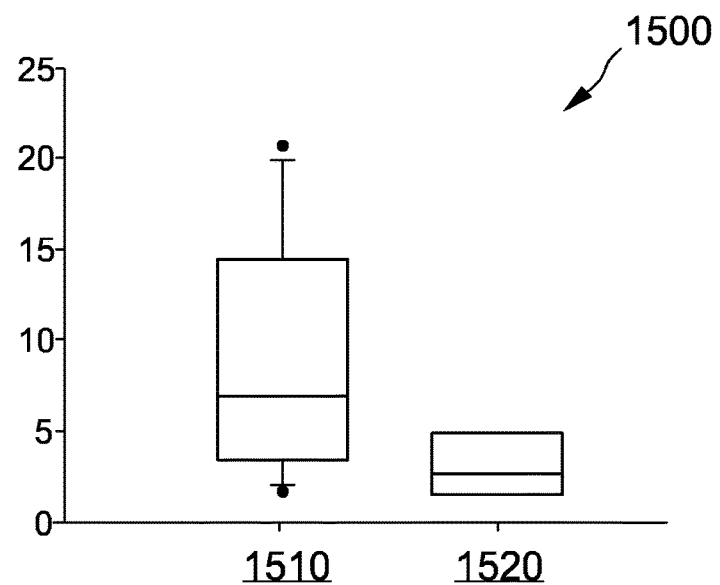
FIGS. 9 and 10 show the absolute daily gradient in the ratio of the mean awake activity count to mean sleep activity count in non-readmitted and readmitted patients and the corresponding ROC curve.
Figure 10:
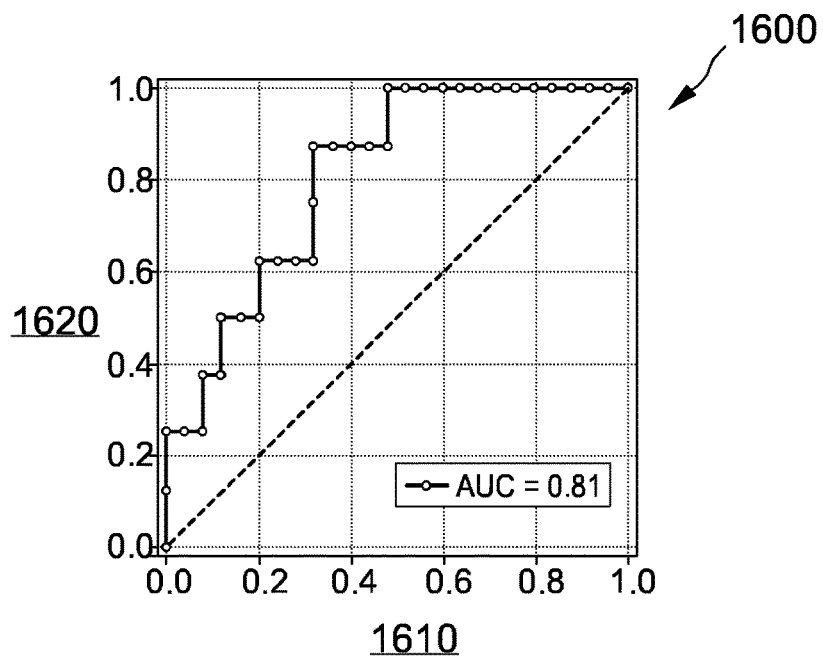

FIGS. 9 and 10 show the absolute daily gradient in the ratio of the mean awake activity count to mean sleep activity count 1500 in non-readmitted 1510 and readmitted patients 1520 in the recovery period, days one to five post-discharge corresponding receiver operating characteristic curve 1600 (displaying sensitivity 1620 over specificity 1610 with an area under the curve AUC of 0.81). The gradient reflects the daily variation in the ratio, with non-readmitted patients having a greater variation than those readmitted. Within the first five days, there is a significant difference in the absolute daily gradient in the ratio between the readmitted and non-readmitted (p<0.02).

Activity parameters in which there are significant differences within the first week post-discharge can be used to stratify patients into levels of risk, to allow for closer monitoring in those patients with a higher risk of an exacerbation resulting in a hospital re-admission.

There is a significant change in some activity parameters before an exacerbation resulting in a hospital re-admission. One example is a parameter derived from Fourier-transformed activity data, the "moment". Herein, a moment is typically defined as the integral of frequency-dependent activity data (obtained by Fourier-transforming time-dependent activity data) between a first and a second frequency.

Figure 11:
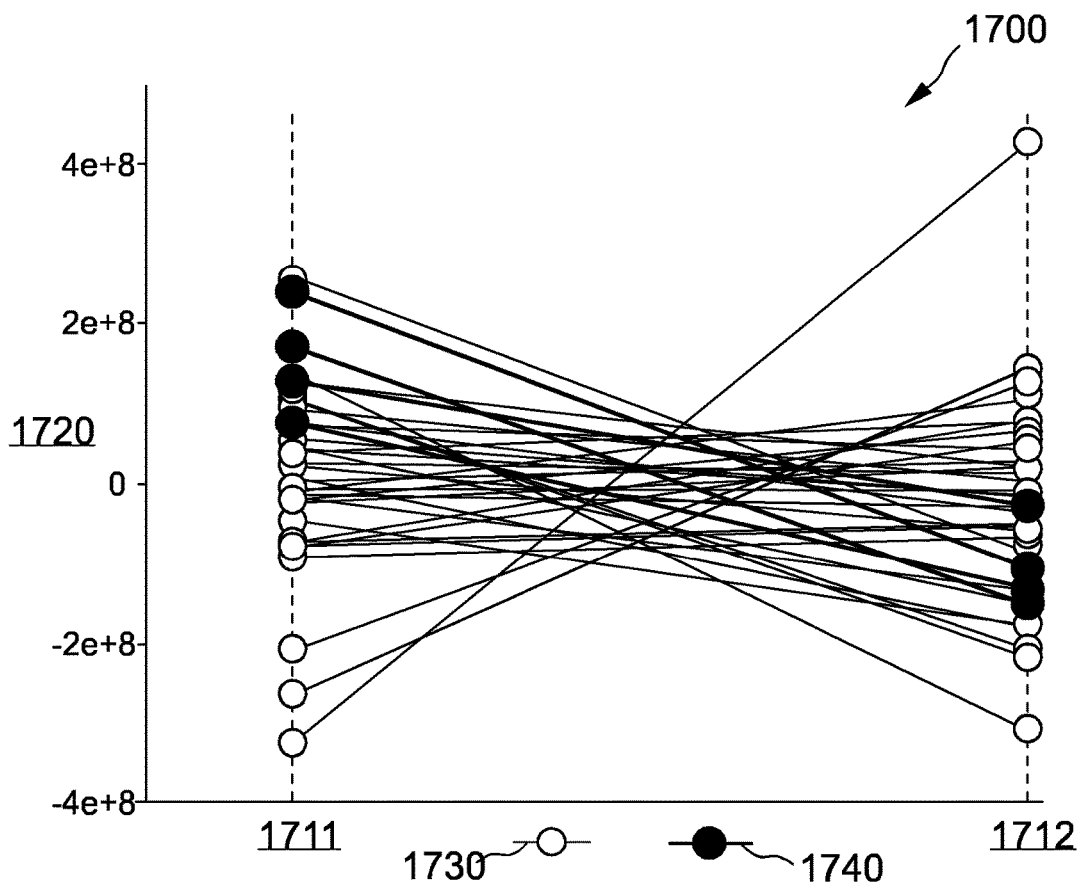
FIG. 11 shows the time evolution of the moment gradient post discharge for readmitted and non-readmitted patients.

Graph 1700 in FIG. 11 shows how the daily gradient 1720 of the moment changes in week one post-discharge (denoted by reference sign 1711) compared to week two post-discharge (denoted by reference sign 1712), in both readmitted patients 1740 and non-readmitted patients 1730. Readmitted patients 1740 have a negative change in the moment gradient 1720 compared to the week before or baseline assessment. Generally, non-readmitted patients 1730 display either a positive change or no change in week two compared to week one. In more detail, FIG. 11 shows an example of how a moment gradient 1720 varies over time (shown on the x-axis of FIG. 11). That is, the y-axis of FIG. 11 shows the change in moment and not the moment itself. A negative moment gradient means that the moment has a decreasing trend. A positive moment gradient means that the moment has an increasing trend. FIG. 11 shows that the daily moment gradient for well-recovering subjects is hardly changing (apart from a few exceptions). Thus, for these patients, a decreasing moment is no cause for alarm as long as the decrease does not "accelerate", i.e., as long as the gradient does not change as well. On the other hand, the moment gradient does change (in fact, it decreases) for patients who were readmitted. Thus, for these patients, the moment decreased faster and faster which can consequently be used to predict an increased risk of an exacerbation or readmission. Data are shown for one week post discharge (line 1711) and for two weeks post discharge (line 1712). Open circles 1730 correspond to data for patients who were not readmitted (i.e., for patients who recovered well). Filled circles 1740 correspond to data for patients who were readmitted within one month post-discharge (i.e., for patients who did not recover well). On average, readmitted patients show a decline in the moment gradient over time, reflecting the lack of variation in the range of activity levels during the week prior to readmission. In contrast, there is no change in the non-readmitted patients between weeks one and two post discharge. The results in FIG. 6 show that there is a significant difference in the moment gradient between weeks one and two for readmitted patients. In addition, although some patients in the non-readmitted group have a similar pattern to the readmitted, there is no significant difference between weeks one and two for non-readmitted patients.

If patients in the higher risk category (e.g., category "medium risk" 1142 or category "high risk" 1143) have a negative change in the moment gradient, this is a potential indication of an upcoming exacerbation and/or an increased risk of hospital re-admission, and an alert will be sent to the clinician, so an appropriate intervention can take place to prevent further deterioration.

If patients in the "low risk" category 1141 have a negative change in the moment gradient, the awake-sleep and Fourier-transform parameters should be examined to reassess the risk category. If there is a strong variation or change in the activity parameters, then an alert can be sent.

In another embodiment, physiological data such as BMI, age, spirometry, history of exacerbation, is collected in the hospital at admission and discharge. It can also be used together with physical activity data to determine a patient's level of risk of an upcoming exacerbation. A similar monitoring system as in the first embodiment may be used.

In yet another embodiment, patient's symptom data can be collected via a questionnaire on a daily basis. Examples of symptoms include breathlessness, coughing, sputum production and sputum color, which in combination with the physical activity monitoring, can be used to assess the risk of an upcoming exacerbation. A similar monitoring system as described with reference to the first embodiment is used.

Figure 12:
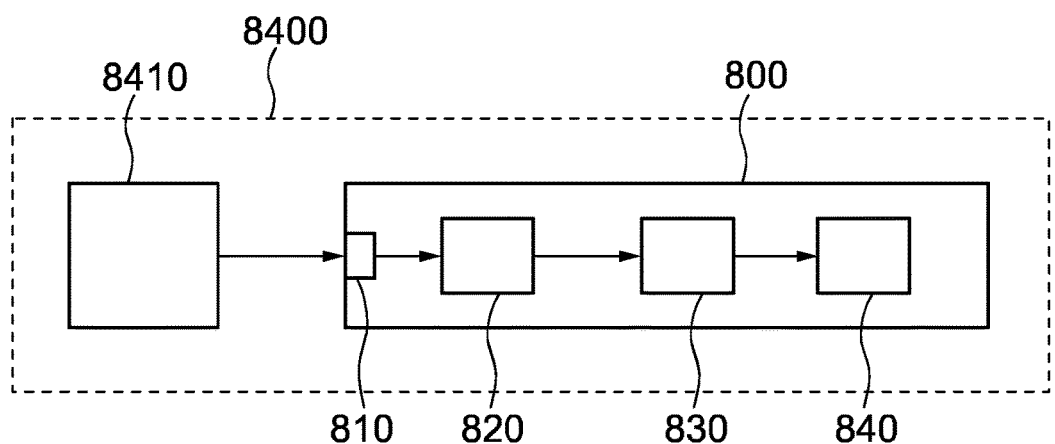
FIG. 12 shows schematically and exemplarily an embodiment of a system for assessing a risk of an exacerbation and/or hospitalization of a subject.

FIG. 12 shows schematically and exemplarily an embodiment of a system 8400 for assessing a risk of an exacerbation and/or hospitalization of a subject. System 8400 comprises a physical activity measurement unit 8410 that is configured to gather time-dependent activity data for said subject. System 8400 further comprises an apparatus 800 for assessing a risk of an exacerbation and/or hospitalization of a subject. Apparatus 800 comprises an input unit 810 for receiving at least time-dependent activity data for said subject. The time-dependent activity data comprises at least first and second activity data. The first activity data is indicative of the subject's physical activity during at least part of an active period of time. The second activity data is indicative of said subject's physical activity during at least part of a rest period of time. Apparatus 800 further comprises an activity data transform unit 820 configured to transform at least part of said time-dependent activity data to obtain frequency-dependent activity data, a moment determination unit 830 that is configured to compute a moment based at least on part of said frequency-dependent activity data; and a risk assessment unit 840 that is configured to assess said risk of said exacerbation and/or hospitalization of said subject based at least on said moment and on whether an expression involving the first activity data and/or the second activity data fulfills a predetermined relationship with respect to a predetermined activity level. Risk assessment unit 840 may however also be configured to assess said risk of said exacerbation and/or hospitalization of said subject based on a subset or all of the respective parameters described herein. Input unit 810 of apparatus 800 is configured to receive said time-dependent activity data from physical activity measurement unit 8410.

Figure 13:
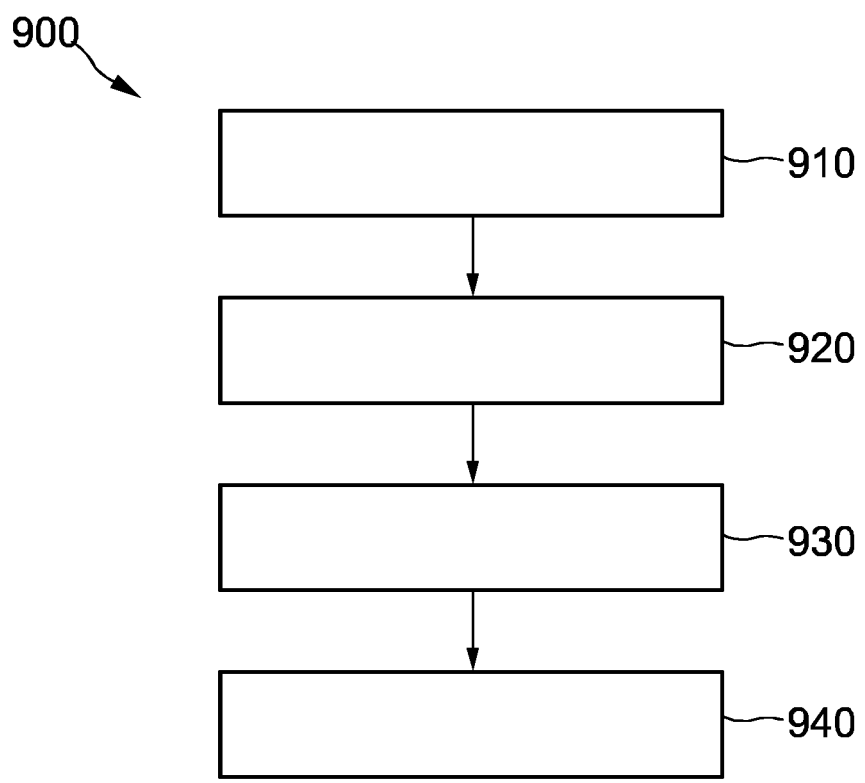
FIG. 13 shows schematically and exemplarily an embodiment of a method for assessing a risk of an exacerbation and/or hospitalization of a subject.

FIG. 13 shows schematically and exemplarily an embodiment of a method 900 for assessing the risk of an exacerbation and/or hospitalization of a subject. In a first step 910, method 900 proposes to receive at least time-dependent activity data for said subject. The time-dependent activity data comprises at least first and second activity data. The first activity data is indicative of the subject's physical activity during at least part of an active period of time. The second activity data is indicative of the subject's physical activity during at least part of a rest period of time. In a second step 920, method 900 proposes to transform at least part of said time-dependent activity data to obtain frequency-dependent activity data. For instance, step 920 may comprise performing a Fourier-transform on said time-dependent activity data to obtain frequency-dependent activity data. In a third step 930, method 900 proposes to compute a moment based at least on part of said frequency-dependent activity data. In a fourth step 940, method 900 proposes to assess said risk of said exacerbation and/or hospitalization of said subject based at least on said moment and on whether an expression involving the first activity data and/or the second activity data fulfills a predetermined relationship with respect to a predetermined activity level.

Preferably, the "first activity level" represents a threshold to which active period activity data (i.e., the first activity data) are compared. In one example, this threshold would be set to a mean active period activity count of a stable patient. That way, if the first activity data are higher than the "first activity level", the patient is more active than an average stable patient during active periods. Likewise, if the first activity data are lower than the "first activity level", the patient is less active than an average stable patient during active periods. The "second activity level" represents a threshold to which rest period activity data (i.e., the second activity data) are compared. In another example (which may be equal to or different from the example referred to above), this threshold would be set to a mean rest period activity count of a stable patient. That way, if the second activity data are higher than the "second activity level", the patient is more active than an average stable patient during rest periods. Likewise, if the second activity data are lower than the "second activity level", the patient is less active than an average stable patient during rest periods. Note that the term "activity level" does not necessarily imply that the "level" is an activity (measured in counts/min). For instance, having regard to the ratio approach described herein above, the "activity level" would correspond to a unit-less number.

A typical application of the present invention would be to assist COPD patients in the home environment. This may be achieved by employing activity monitoring devices. The present invention may further be applied as part of a feedback component for a coaching (or personal trainer) system. The present invention is specifically designed for use in COPD, but it can also be used for other chronic diseases, where staying active is important. The present invention is useful in the context of respiratory diseases, including COPD, neuromuscular disorders and other chronic diseases like cardiovascular diseases, heart failure, and for elderly patients with cognitive diseases as well as diabetes.

The apparatus can comprise storage means for storing the received activity data. The apparatus can further comprise wireless receiver means such as, e.g., an antenna for receiving the physical activity data. Additionally and/or alternatively, the physical activity measurement unit may comprise storage means for storing the physical activity measurement data. Further, the apparatus and/or the physical activity measurement unit may have read and/or write access to read physical activity data from and write physical activity data to a database.

Although in the above described embodiments, the risk assessment unit and the moment determination unit are comprised in the same apparatus, these embodiments are preferred embodiments only and in another embodiment the moment determination unit may be arranged within the physical activity measurement unit. Further, transforming the time-dependent activity data to frequency space and computing the moment may be performed by a unit separate from the physical activity measurement unit and separate from the risk assessment unit.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like computing moments of the frequency-dependent activity data et cetera performed by one or several units or devices can be performed by any other number of units or devices. The determinations and/or the control of the apparatus in accordance with the above described method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The present invention relates to an apparatus, a system, a method, and a computer program for assessing the risk of an exacerbation and/or hospitalization. According to some embodiments, a patient's physical activity is measured (e.g., by an accelerometer) during an active period of time (e.g., during awake hours) and during a rest period of time (e.g., during sleep hours) to gather first and second activity data. A risk of exacerbation and/or hospitalization is assessed (e.g., by a risk assessment unit) based on based at least on said moment and on whether an expression involving the first activity data and/or the second activity data fulfills a predetermined relationship with respect to a predetermined activity level. For instance, lack of daily moment variation as well as low activity data during active periods and high activity data during rest periods indicates an increased risk of exacerbation and/or hospital readmission for the patient.

Chronic obstructive pulmonary disease (COPD) is one of the growing chronic respiratory diseases and is now a major cause of morbidity and mortality. Acute exacerbations have a negative impact on health related quality of life of COPD patients, survival rates, pulmonary function and utilization of health-care resources. The present application discloses an apparatus 100, system 1400, method 200, and computer program for assessing a risk of an exacerbation and/or hospitalization of a subject. To this extent, time-dependent activity data is Fourier-transformed to frequency space to obtain frequency-dependent activity data. Next, a moment of said frequency-dependent activity data is computed. Finally, a risk of said exacerbation and/or hospitalization of said subject to occur is assessed based on said moment.

The invention claimed is:

1. A monitoring apparatus for assessing a risk of an exacerbation and/or hospitalization of a subject, the apparatus comprising:
an input unit for receiving time-dependent physical activity data for a subject, the time-dependent physical activity data being obtained by an accelerometer;
an activity data transform unit configured to transform the time-dependent activity data to obtain frequency-dependent activity data;
a moment determination unit configured to compute a moment of the frequency-dependent activity data;
a risk assessment unit configured to assess a risk of exacerbation and/or hospitalization of the subject based at least on the moment of the frequency, wherein the moment of the frequency-dependent activity data corresponds to an integral of the frequency-dependent activity data over all frequencies, and/or wherein the moment of the frequency-dependent activity data corresponds to an integral of the frequency-dependent activity data between a first frequency and a second frequency; and
a warning unit, configured to provide a warning indication based on the assessed risk of exacerbation and/or hospitalization of the patient.

2. The apparatus as defined in claim 1, wherein the risk assessment unit is configured to identify an increased risk of exacerbation and/or hospitalization of the subject if a moment for the subject corresponding to activity data gathered on a first day is greater than a moment for the subject corresponding to activity data gathered on a second day, the first day being prior to the second day.

3. The apparatus as defined in claim 1, wherein the risk assessment unit is configured to compare a first moment to a second moment, where the first moment corresponds to activity data gathered during a first time period on a first day, where the second moment corresponds to activity data gathered during a second time period on a second day.

4. The apparatus as defined in claim 1, wherein said risk assessment unit is configured to assess said risk of said exacerbation and/or hospitalization of said subject based on a moment gradient.

5. The apparatus as defined in claim 4, wherein said moment gradient corresponds to a change in moment for said subject from a first day to a second day, said first day being prior to said second day.

6. The apparatus as defined in claim 1, wherein said moment of said frequency-dependent activity data corresponds to a center-of-gravity of said frequency-dependent activity data.

7. The apparatus as defined in claim 1, wherein the time-dependent activity data corresponds to activity data as a function of time gathered during a first time period.

8. The apparatus as defined in claim 1, wherein the input unit is configured for receiving time-dependent activity data comprising at least first and second activity data; wherein the first activity data is obtained by means of the accelerometer and indicative of the subject's physical activity during at least part of an active period of time; wherein the second activity data is obtained by means of the accelerometer and indicative of the subject's physical activity during at least part of a rest period of time; and the risk assessment unit is configured to assess the risk of exacerbation and/or hospitalization of the subject based at least on the moment and on whether an expression involving the first activity data and/or the second activity data fulfills a predetermined relationship with respect to a predetermined activity level.

9. The apparatus of claim 8, configured to compare the first activity data to a first activity level; and/or wherein the apparatus is configured to compare the second activity data to a second activity level.

10. The apparatus of claim 9, wherein the predetermined relationship comprises the conditions that (1) the first activity data is lower than the first activity level, and (2) the second activity data is higher than the second activity level.

11. The apparatus of claim 8, wherein the apparatus is configured to determine a ratio between first activity data and second activity data.

12. The apparatus of claim 8, wherein the apparatus is configured to determine a difference between first activity data and second activity data.

13. A system for assessing a risk of an exacerbation and/or hospitalization of a subject, the system comprising:
a physical activity measurement unit that is configured to gather time-dependent physical activity data for the subject by means of an accelerometer; and
an apparatus as defined in claim 1; wherein the input unit of the apparatus is configured to receive the time-dependent activity data from the physical activity measurement unit.

14. A method for assessing a risk of an exacerbation and/or hospitalization of a subject, the method comprising:
receiving time-dependent physical activity data for the subject obtained by an accelerometer;
transforming the time-dependent activity data to obtain frequency-dependent activity data;
computing a moment of the frequency-dependent activity data;
assessing the risk of the exacerbation and/or hospitalization of the subject based at least on the moment, wherein the moment of the frequency-dependent activity data corresponds to an integral of the frequency-dependent activity data over all frequencies, and/or wherein the moment of the frequency-dependent activity data corresponds to an integral of the frequency-dependent activity data between a first frequency and a second frequency; and
providing a warning indication based on the assessed risk of exacerbation and/or hospitalization of the patient.

15. A system for facilitating computer-assisted patient monitoring, the system comprising one or more processors configured by instructions that cause the one or more processors to perform the steps of:
receiving, with the one or more processors, time-dependent physical activity data for the subject obtained by an accelerometer;
transforming, with the one or more processors, the time-dependent activity data to obtain frequency-dependent activity data;
computing, with the one or more processors, a moment of the frequency-dependent activity data;
assessing, with the one or more processors, the risk of the exacerbation and/or hospitalization of the subject based at least on the moment, wherein the moment of the frequency-dependent activity data corresponds to an integral of the frequency-dependent activity data over all frequencies, and/or wherein the moment of the frequency-dependent activity data corresponds to an integral of the frequency-dependent activity data between a first frequency and a second frequency; and
providing, with the one or more processors, a warning indication based on the assessed risk of exacerbation and/or hospitalization of the patient.

* * * * *